(12) United States Patent
Murata et al.

(10) Patent No.: US 10,751,271 B2
(45) Date of Patent: Aug. 25, 2020

(54) FAST RINSING CLEANSING COMPOSITION

(71) Applicant: Conopco, Inc., Englewood Cliffs, NJ (US)

(72) Inventors: Yukihiro Murata, Saitama (JP); Kazuki Uyama, Kawasaki (JP)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 15/549,812

(22) PCT Filed: Feb. 10, 2016

(86) PCT No.: PCT/EP2016/052781
§ 371 (c)(1),
(2) Date: Aug. 9, 2017

(87) PCT Pub. No.: WO2016/131687
PCT Pub. Date: Aug. 25, 2016

(65) Prior Publication Data
US 2018/0021233 A1    Jan. 25, 2018

(30) Foreign Application Priority Data

Feb. 19, 2015    (EP) ..................................... 15155828

(51) Int. Cl.
| | |
|---|---|
| *A61K 8/00* | (2006.01) |
| *A61K 8/37* | (2006.01) |
| *A61K 8/31* | (2006.01) |
| *A61K 8/34* | (2006.01) |
| *A61K 8/49* | (2006.01) |

(Continued)

(52) U.S. Cl.
CPC .................. *A61K 8/37* (2013.01); *A61K 8/31* (2013.01); *A61K 8/345* (2013.01); *A61K 8/4973* (2013.01); *A61K 8/86* (2013.01); *A61K 8/89* (2013.01); *A61Q 1/14* (2013.01); *A61Q 19/10* (2013.01)

(58) Field of Classification Search
None
See application file for complete search history.

(56) References Cited

U.S. PATENT DOCUMENTS

| | | |
|---|---|---|
| 3,424,849 A | 1/1969 | Conklin et al. |
| 4,488,564 A | 12/1984 | Grollier et al. |

(Continued)

FOREIGN PATENT DOCUMENTS

| | | |
|---|---|---|
| CA | 2776366 | 4/2011 |
| CN | 1051671 | 5/1991 |

(Continued)

OTHER PUBLICATIONS

IPRP in PCTEP2016052781, Apr. 24, 2017.

(Continued)

*Primary Examiner* — Necholus Ogden, Jr.
(74) *Attorney, Agent, or Firm* — Edward A. Squillante, Jr.

(57) ABSTRACT

A cleansing composition is provided for removing waxy makeup, and for cleansing the skin with excellent rinse speed and after-feel. The inventive composition is also transparent and stable to phase separation and includes specific amounts of high average HLB nonionic surfactants, specific alkyl mono esters, hydrocarbon oils and polyol(s) and in a preferred embodiment contains very low levels of or no silicone oils.

10 Claims, 3 Drawing Sheets

(51) Int. Cl.

| | | |
|---|---|---|
| *A61Q 1/14* | (2006.01) | |
| *A61K 8/86* | (2006.01) | |
| *A61Q 19/10* | (2006.01) | |
| *A61K 8/89* | (2006.01) | |

(56) References Cited

U.S. PATENT DOCUMENTS

| | | | |
|---|---|---|---|
| 4,659,820 | A | 4/1987 | Fauss et al. |
| 5,011,681 | A | 4/1991 | Ciotti et al. |
| 5,578,299 | A | 11/1996 | Starch |
| 5,712,232 | A | 1/1998 | Moriyama et al. |
| 5,888,492 | A | 3/1999 | Starch |
| 2002/0012643 | A1 | 1/2002 | Ramin et al. |
| 2004/0136943 | A1 | 7/2004 | Tomokuni |
| 2005/0180942 | A1 | 8/2005 | Shimizu |
| 2005/0192190 | A1 | 9/2005 | Hasenzahl et al. |
| 2005/0238680 | A1 | 10/2005 | Stella et al. |
| 2008/0293603 | A1 | 11/2008 | Watanabe et al. |
| 2014/0142016 | A1 | 5/2014 | Tomokuni et al. |
| 2014/0142203 | A1 | 5/2014 | Tezuka et al. |
| 2014/0155353 | A1 | 6/2014 | Tezuka et al. |

FOREIGN PATENT DOCUMENTS

| | | | |
|---|---|---|---|
| CN | 101234069 | | 8/2008 |
| CN | 101797212 | | 8/2010 |
| CN | 101919788 | | 12/2010 |
| CN | 103648474 | | 3/2014 |
| EP | 1488775 | | 12/2004 |
| EP | 1952795 | * | 6/2008 |
| EP | 1952795 | | 4/2015 |
| JP | 9124438 | | 5/1997 |
| JP | 1135421 | | 2/1999 |
| JP | 2001270807 | | 10/2001 |
| JP | 3441261 | | 8/2003 |
| JP | 2003252726 | | 10/2003 |
| JP | 2003286134 | | 10/2003 |
| JP | 2004231543 | | 8/2004 |
| JP | 2005112751 | | 4/2005 |
| JP | 2007254573 | | 10/2007 |
| JP | 2008105989 | | 5/2008 |
| JP | 2008115137 | | 5/2008 |
| JP | 2010001231 | | 1/2010 |
| JP | 2010090111 | | 4/2010 |
| JP | 4763474 | | 8/2011 |
| JP | 2012107147 | | 6/2012 |
| JP | 2012206974 | | 10/2012 |
| JP | 2014231501 | | 12/2014 |
| WO | WO2007089100 | | 8/2007 |

OTHER PUBLICATIONS

Search Report in EP15155828, dated Jul. 22, 2015, EP.
Written Opinion in EP15155828, dated Jul. 22, 2015.
Written Opinion in PCTEP2016052781, dated Jan. 5, 2017.

* cited by examiner

- Smoothness of testers is evaluated by mean friction coefficient (MIU)
- Sensor with silicone rubber reproducing the surface asperities of human finger tip
- Sample table topped with artificial leather imitating human skin Apparatus: Friction Tester KES-SE
(Kato tech Co., Ltd.)

Theoretical Formula for Calculation of MIU

FAST RINSING CLEANSING COMPOSITION

BACKGROUND OF THE INVENTION

Field of the Invention

The invention concerns a cleansing composition, in particular a make-up removing cosmetic composition of improved efficacy and rinse speed. In particular, it relates to a composition that removes makeup efficiently with excellent skin feel attributes.

Background of the Art

An important segment of the cosmetics market are makeup removal products ("MURs") which are utilized for removing make-up by consumers. Removal of pigments of eye shadow, mascara, blush, lipstick and face powder is a daily problem for many women. The problem has been addressed through formulations which may include materials operating by solvent action or by emulsification. However, such cleansers often have disadvantages that they are slow rinsing and/or have negative skin feel attributes and may tend to phase separate over time i.e. they are not stable. Specifically high oil containing MURs have high make up removability but their slow rinsing speed and residual feeling are not preferred by many consumers. It is known that high oil make up removers must include high levels of low HLB nonionic surfactants to stabilize the high level of oil ingredients (typically 45%-80 wt. %) in the formulation for efficient make up removability. However it is also well known that high levels of low HLB nonionic surfactants leads to slow rinsing speed and often has a deleterious residual feeling on the skin.

U.S. Patent Publication No. 2005/0180942 published on Aug. 18, 2005 to Shimizu et al. describes a cleansing composition containing nonionic surfactants selected from various glycerol fatty acid esters in an oil base and having specific IOB values. The formulation is reported to resist phase separation.

U.S. Patent Publication No. 2004/0136943 published on Jul. 15, 2004 to Tomokuni describes a cleansing composition comprising (A) an oil component, (B) a hydrophilic nonionic surfactant, (C) a lipophilic amphiphile, (D) a water soluble solvent and (E) water. The composition reportedly has an isotropic liquid phase exhibiting a bicontinuous structure. The composition is described as exhibiting excellent detergency for the removal of both oil stains and water soluble stains and has high rinsability.

Various silicone oils have been used in the past to improve the sticky skin feeling from these products. Surprisingly the present inventive oil make up remover contains low levels of a high HLB nonionic surfactant and selected specific alkyl mono ester(s) and was seen to improve the rinsing speed and residual skin sensory feeling preferably without using silicone oils. Moreover it still was observed to stabilize high levels of hydrocarbon oil with excellent product transparency and stability.

Preferably the inventive product is used with a countertop mechanical pump that may be situated in a stable position so that the hand or forearm can be used to depress the pump and dispense the product. This arrangement results in a convenient and hygienic cleansing process.

BRIEF DESCRIPTION OF THE INVENTION

In one aspect of the invention is a cleansing composition including but not limited to:

a. about 10 to 25 wt. % of nonionic surfactant(s) collectively having a weight average HLB greater than 10.8.
b. about 20 to 40 wt. % of linear and/or branched C5 to C 20 alkyl mono ester(s) where the molecular weight of the ester(s) is/are less than 320.
c. about 25 to 40 wt. % of hydrocarbon oil(s);
d. about 8 to 30 wt. % of polyol(s); and
e. about 1 to 10 wt. % of water.

Definitions

"Weight average HLB" is calculated referring to "The Atlas HLB Surfactant Selector",
Griffin, W. C. (1949) J. Soc. Cosmet. Chem. 1:311-26

HLB average=Σ(Nonionic surfactant HLB×concentration)/total Nonionic surfactant concentration.

More specifically, as explained in Griffin, when two or more surfactants (emulsifiers) are combined (for our invention this relates specifically to combination of nonionic surfactants), the weight average HLB is the sum of the HLB value of each nonionic surfactant weighted by the concentration of each relative to overall concentration of nonionic surfactant. Thus, for example, if we were to blend three parts of a nonionic surfactant having HLB of 8 with one part of a nonionic surfactant having an HLB of 16, the weighted HLB average would be (¾) (8)+(¼) (16)=6+4=10.

Transparent means a turbidity of 0.05 optical density (OD) or less at 25 C measured at 500 nm using a 1 cm glass cell and a U-2810 spectrophotometer (Hitachi) or equivalent measured against distilled or deionized water as reference.

Stable means no phase separation after storage during 90 days at 45 C (in the dark).

Rinsing speed means either slow, moderate or fast rinsing of the product off the skin with water as judged by an expert panel using the test procedure described below.

DETAILED DESCRIPTION OF THE INVENTION

Figure 1:
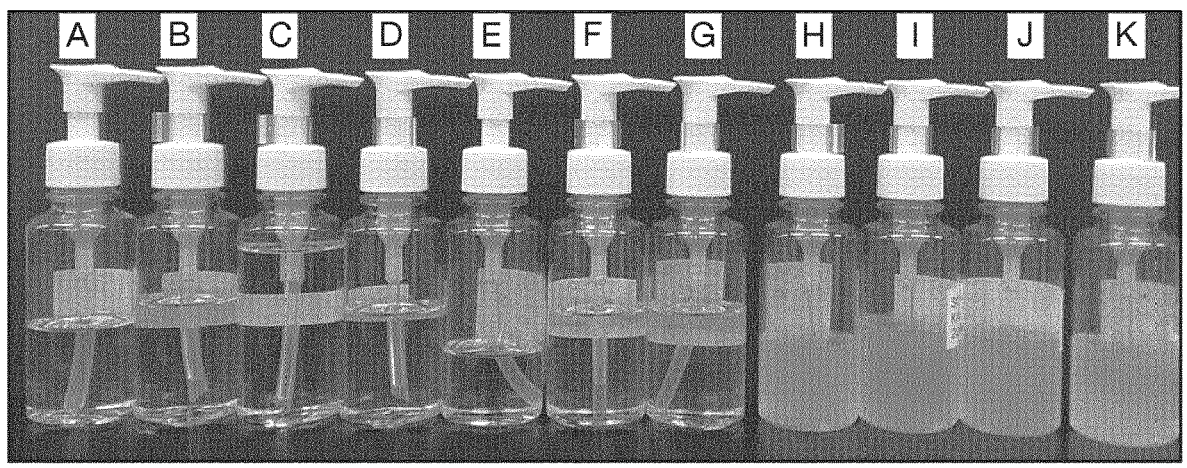
FIG. 1 is a photograph showing the comparative phase stability of inventive vs. comparative compositions.
Figure 2:
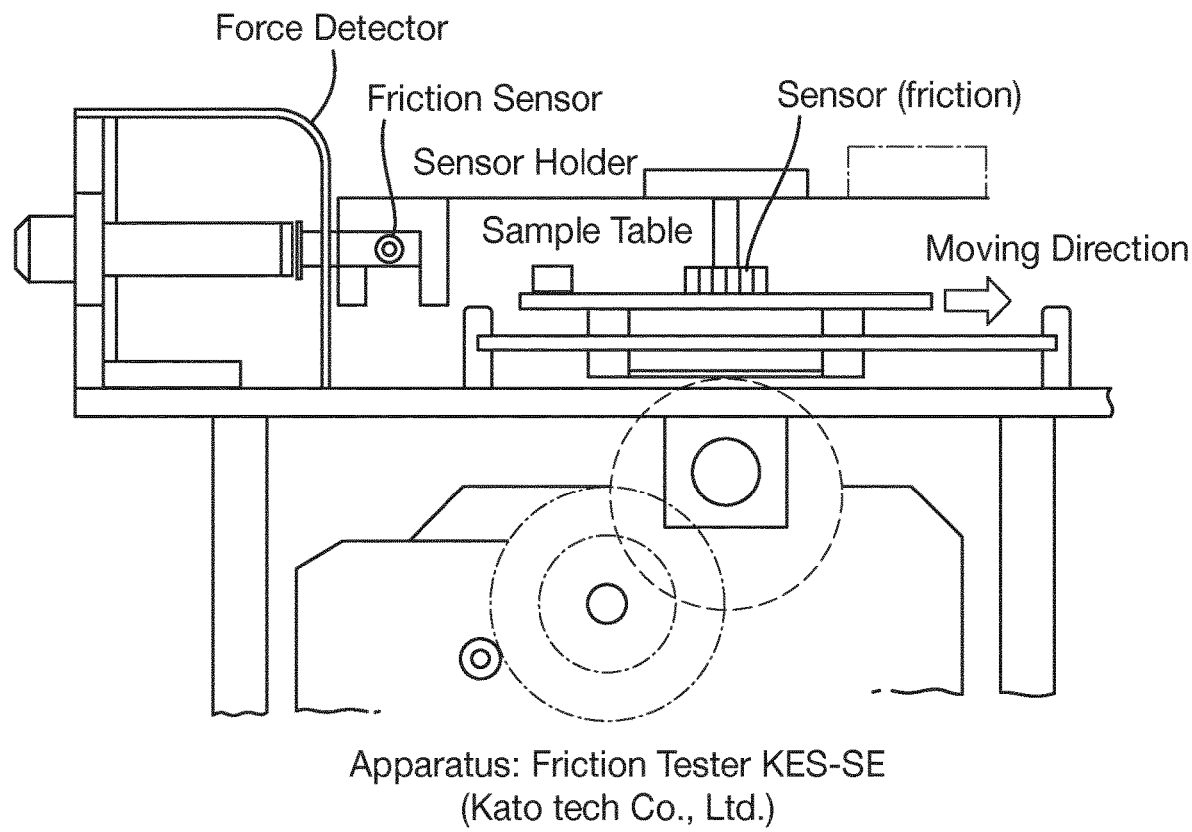
FIG. 2 is a schematic diagram of a KES-SE friction tester manufactured by Kato Tech Co., Ltd. (Kyoto, Japan) that is useful to determine the MIU frictional value of selected compounds. MIU is defined as the average value of μ or frictional coefficient measured in a distance of 20 mm with the KES-SE friction tester using the procedure provided below.

All publications and patent applications, patents, and other references mentioned herein are incorporated by reference in their entirety.

In one aspect of the invention is a cleansing composition including but not limited to:

a. about 10 to 25 wt. % of nonionic surfactant(s) collectively having a weight average HLB greater than 10.8, preferably greater than 11.0; preferably the concentration of nonionic surfactant(s) are in a maximum of about 23 wt. %, and a minimum of about 13 wt. %;
b. about 20 to 40 wt. % of linear and/or branched C5 to C20 alkyl mono ester(s) where the molecular weight of the ester(s) is/are less than 320, preferably present at a minimum of about 23 and a maximum of about 33 wt. %; preferably where the maximum alkyl number is 18;

c. about 25 to 40 wt. % of hydrocarbon oil(s) (preferably the hydrocarbon oil(s) comprise at least 50 wt. % Mineral oil based on the total oil content); preferably the hydrocarbon oil(s) have a maximum concentration of about 35 wt. %, and a minimum concentration of about 27 wt. %);

d. about 8 to 30 wt. % polyol(s) (preferably a maximum concentration of about 20 wt. % and a minimum concentration of about 10 wt. %).

e. about 1 to 10 wt. % of water (preferably a maximum concentration of about 8 wt. % and a minimum concentration of about 4 wt. %);

Advantageously the alkyl mono ester(s) have an average frictional coefficient upon application to the skin of less than 0.3 MIU as measured by the standard friction coefficient method described herein. Preferably the inventive composition further includes less than 1.0 wt. % of a silicone oil(s); preferably less than 0.5 wt. % and more preferably less than 0.1 or 0.01 or 0.001 wt. % of silicone oil(s).

Preferably at least 50 wt. % the total alkyl mono ester(s) is/are selected from Isodecyl Neopentanoate, Ethylhexyl Isononanoate, Isopropyl Myristate or blends thereof. More preferably at least 50 wt. % of the total polyol(s) are selected from propylene glycol, 1,3-Butylene Glycol, Dipropylene glycol or blends thereof.

Advantageously the inventive composition is transparent, preferably determined immediately after its preparation. Preferably the composition is stable. More preferably the composition has a viscosity in the range of 1 to 200 cps, preferably 10 to 150 cps at 25 C using the standard viscosity method. Most preferably the composition is a make-up remover composition.

Advantageously the invention is a packaged product for removing makeup from the skin comprising the above composition contained within a pump dispenser.

Nonionic Surfactants:

The inventive cleansing composition contains one or more nonionic surfactant(s) collectively having a weight average HLB greater than 10.8 (preferably greater than 11.0).

A variety of nonionic surfactants may be employed in the present invention as long as they collectively and preferably have the above weight average HLB value. Nonionic surfactants do not include linear and/or branched C5 to C 20 alkyl mono ester(s) with a molecular weight not exceeding 320. Particularly preferred nonionic surfactants are those with a $C_{10}$-$C_{20}$ fatty alcohol or acid hydrophobe condensed with from about 2 to about 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides are also suitable nonionic surfactants.

Useful materials also include POE-20 sorbitan monolaurate; POE-20 cetyl ether; POE-7 glyceryl cocoate; POE-15 stearyl ether; POE-10 stearyl ether; POE-15 palmityl ether; PEG-75 Stearate and combinations thereof. Other useful nonionic surfactants are alkyl polyglycosides such as lauryl polyglucoside available from the Henkel Corporation. Another class of nonionic surfactants are the long chain tertiary amine oxides.

Alkyl Mono Esters:

The inventive cleansing composition contains alkyl mono ester(s) comprising linear and/or branched alkyl mono ester(s) not exceeding an alkyl number of 20 where the molecular weight of the ester(s) is/are less than 320. Preferably the minimum alkyl chain length is 5. Examples of alkyl mono esters useful in the invention include, but are not limited to, one or more of the following: isodecyl neopentanoate, ethylhexyl isononanoate, isopropyl myristate, blends thereof and the like. Such alkyl mono esters may be obtained from the following suppliers:

Isodecyl Neopentanoate,

NEOLIGHT 100P, IPM-R, and ES108109 available from (Kokyu Alcohol Kogyo Co. Ltd, Narita, Chiba, Japan); DUB VCI-10 available from (Stearinerie Dubois, Boulogne-Billancourt, France)

Ethylhexyl Isononanoate,

ES108109 available from (Kokyu Alcohol Kogyo Co. Ltd, Narita, Chiba, Japan); EMALEX NIO-98 available from (Nihon Emulsion Co. Ltd, Tokyo, Japan)

Isopropyl Myristate

IPM-R available from (Kokyu Alcohol Kogyo Co. Ltd, Narita, Chiba, Japan);

IPM available from BASF SE, Ludwigshafen, Germany)

Hydrocarbon Oils:

The inventive cleansing composition contains hydrocarbon oil(s). Hydrocarbon oil(s) suitable for the present invention include mineral oil, isoparaffins and poly alpha-olefins (such as those available under the trademark Permethyl 99A or 101), and polyisobutenes.

Preferably these oils have a coefficient of kinematic viscosity not exceeding 300 (mm2/s) at 25° C. as determined using a Brookfield Model LVDV-II+ viscometer.

Examples of oils useful in the invention include one or more of the following: Mineral oil, Liquid paraffin, Squalene, blends thereof and the like. Useful oils include the following: Carnation and Blandol mineral oils available from Sonneborn LLC, Parsippany N.J., USA; Rajol WP 70 liquid paraffin available from Raj Petro Specialties P.LTD, Mumbai, India; and Parleam 4 Hydrogenated Polyisobutene (C13-16 Isoparaffin), EX and 6 Hydrogenated Polyisobutenes all available from NOF CORPORATION, Japan.

Polyols

Polyols are preferably present in compositions of this invention. These polyols may be monomeric or polymeric and are preferably liquid at 25 C. Monomeric polyols may have from 1 to 20 carbon atoms and from 2 to 10 hydroxyls. Illustrative monomeric polyols include glycerine, propylene glycol; glycerol; 1,4-butane diol; 1,3-butane diol; 1,2-butane diol; 1-6-hexanediol, 1,2-hexane diol; 3-methyl-1,3-butane diol; 2-methyl-1,3-propane diol, sorbitol and mixtures thereof. Particularly preferred are glycerin, propylene glycol, and 1,3-butane diol. Polymeric polyols are illustrated by polypropylene glycol, polyethylene glycol, dipropylene glycol, diglycerol, polyglycerol, trimethylene glycol, dipentaerythritol and combinations thereof.

Miscellaneous Agents

Thickening agents may optionally be included in compositions of the present invention. Particularly useful are the polysaccharides. Examples include starches, natural/synthetic gums and cellulosics. Representative of the starches are chemically modified starches such as sodium hydroxypropyl starch phosphate and aluminum starch octenylsuccinate. Tapioca starch is often preferred. Suitable gums include xanthan, *sclerotium*, pectin, karaya, arabic, agar, guar, carrageenan, alginate and combinations thereof. Suitable cellulosics include hydroxypropyl cellulose, hydroxypropyl methylcellulose, ethylcellulose and sodium carboxy methylcellulose. Synthetic polymers are yet another class of effective thickening agent. This category includes cross-linked polyacrylates such as the Carbomers, polyacrylamides such as Sepigel® 305 and taurate copolymers such as Simulgel EG® and Aristoflex® AVC, the copolymers being identified by respective INCI nomenclature as Sodium Acrylate/Sodium Acryloyldimethyl Taurate and Acryloyl Dimethyltaurate/Vinyl Pyrrolidone Copolymer. Another preferred synthetic polymer suitable for thickening is an acrylate-based polymer made commercially available by Seppic and sold under the name Simulgel INS100.

Amounts of the thickener, when used, may range from about 0.001 to about 5%, and preferably, from about 0.1 to about 3%, and most preferably, from about 0.2 to about 1.5% by weight of the composition including all ranges subsumed therein.

Fragrances, colorants, fixatives and abrasives may optionally be included in compositions of the present invention. Each of these substances may range from about 0.05 to about 5%, preferably between 0.1 and 3% by weight.

Turning to the actives suitable for use herein, the same can include opacifiers like $TiO_2$ and ZnO and colorants like iron oxide red, yellow and black. Such opacifiers and colorants typically have a particle size from 50 to 1200 nm, and preferably, from 50 to 350 nm.

To enhance skin moisturization, actives classified as cationic ammonium compounds may optionally be used in the compositions of this invention. Such compounds include salts of hydroxypropyltri ($C_1$-$C_3$ alkyl) ammonium mono-substituted-saccharide, salts of hydroxypropyltri ($C_1$-$C_3$ alkyl) ammonium mono-substituted polyols, dihydroxypropyltri ($C_1$-$C_3$ alkyl) ammonium salts, dihydroxypropyldi ($C_1$-$C_3$ alkyl) mono(hydroxyethyl) ammonium salts, guar hydroxypropyl trimonium salts, 2,3-dihydroxypropyl tri($C_1$-$C_3$ alkyl or hydroxalkyl) ammonium salts or mixtures thereof. In a most preferred embodiment and when desired, the cationic ammonium compound employed in this invention is the quaternary ammonium compound 1,2-dihydroxypropyltrimonium chloride. If used, such compounds typically make up from about 0.01 to about 30%, and preferably, from about 0.1 to about 15% by weight of the composition.

It is preferred that the composition comprises cationic compounds in combination with moisturizing agent. These moisturizing agents may include substituted ureas like hydroxymethyl urea, hydroxyethyl urea, hydroxypropyl urea; bis(hydroxymethyl) urea; bis(hydroxyethyl) urea; bis(hydroxypropyl) urea; N,N'-dihydroxymethyl urea; N,N'-dihydroxyethyl urea; N,N'-di-hydroxypropyl urea; N,N,N'-trihydroxyethyl urea; tetra(hydroxymethyl) urea; tetra(hydroxyethyl) urea; tetra(hydroxypropyl) urea; N-methyl-N'-hydroxyethyl urea; N-ethyl-N,N—N'-hydroxyethyl urea; N-hydroxypropyl-N'-hydroxyethyl urea and N,N'-dimethyl-N-hydroxyethyl urea or mixtures thereof. Where the term hydroxypropyl appears, the meaning is generic for either 3-hydroxy-n-propyl, 2-hydroxy-n-propyl, 3-hydroxy-i-propyl or 2-hydroxy-i-propyl radicals. Most preferred is hydroxyethyl urea. The latter is available as a 50% aqueous liquid from the National Starch & Chemical Division of ICI under the trademark Hydrovance.

Amounts of substituted urea, when used, in the composition of this invention range from about 0.01 to about 20%, and preferably, from about 0.5 to about 15%, and most preferably, from about 2 to about 10% based on total weight of the composition and including all ranges subsumed therein.

It is highly preferred that in particular when cationic ammonium compound(s) and substituted urea(s) are used, at least from about 1 to about 15% glycerin is used, based on total weight of the composition and including all ranges subsumed therein.

Compositions of the present invention may include vitamins as the desired active. Illustrative vitamins are Vitamin A (retinol) as well as retinol esters like retinol palmitate and retinol propionate, Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. Total amount of vitamins when present in compositions according to the present invention may range from 0.001 to 10%, preferably from 0.01% to 1%, optimally from 0.1 to 0.5% by weight of the composition.

Azelaic acid, ubiquinone, dihydroxyacetone (DHA) and mixtures thereof may also be used as actives in the composition of this invention. Such compounds, when used, typically make up from about 0.2 to 4.5%, and preferably, from about 0.5 to 3% by weight of the composition, including all ranges subsumed therein.

Other optional actives suitable for use in this invention include resveratrol, resorcinols like 4-ethyl resorcinol, 4-hexyl resorcinol, 4-phenylethyl resorcinol, dimethoxytoluyl propyl resorcinol, 4-cyclopentyl resorcinol, 4-cyclohexylresorcinol, alpha-an/or beta-hydroxyacids, phenylethyl resorcinol (Symwhite 377 from Symrise), undecylenol phenylalanine (Seppi White from Seppic) mixtures thereof or the like. Such actives, when used, collectively make up from about 0.001 to about 12% by weight of the composition.

Desquamation promoters may be present. Illustrative are the alpha-hydroxycarboxylic acids, beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic and its derivatives, lactic and malic acids. Salicylic acid is representative of the beta-hydroxycarboxylic acids. Amounts of these materials when present may range from about 0.01 to about 15% by weight of the composition.

A variety of herbal extracts may optionally be included as actives in compositions of this invention. The extracts may either be water soluble or water-insoluble carried in a solvent which respectively is hydrophilic or hydrophobic. Water and ethanol are the preferred extract solvents. Illustrative extracts include those from green tea, yarrow, chamomile, licorice, aloe vera, grape seed, citrus unshui, willow bark, sage, thyme and rosemary. Soy extracts may be used and especially when it is desirable to include retinol.

Also optionally suitable for use include materials like chelators (e.g., EDTA), $C_{8-22}$ fatty acid substituted saccharides, lipoic acid, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B and Ceramide 6) as well as pseudoceramides may also be useful. Occlusives like Oilwax LC are often desired. Amounts of these materials may range from about 0.000001 to about 10%, preferably from about 0.0001 to about 1% by weight of the composition.

Sunscreen actives may also be included in compositions of the present invention as described herein. Particularly preferred are such materials as phenylbenzimidazole sulfonic acid (Ensulizole), ethylhexyl p-methoxycinnamate, available as Parsol MCX®, Avobenzene, available as Parsol 1789® and benzophenone-3, also known as Oxybenzone. Inorganic sunscreen actives may be employed such as microfine titanium dioxide, zinc oxide, polyethylene and various other polymers. Also suitable for use is octocrylene. Amounts of the sunscreen agents when present may generally range from 0.1 to 30%, preferably from 0.5 to 20%, optimally from 0.75 to 10% by weight.

Conventional buffers/pH modifiers may be used. These include commonly employed additives like sodium hydroxide, potassium hydroxide, hydrochloric acid, citric acid and citrate/citric acid buffers. In an especially preferred embodiment, the pH of the composition of this invention is from about 4 to about 8, and preferably, from about 4.25 to about 7.75, and most preferably, from about 6 to about 7.5, including all ranges subsumed therein. The Brookfield viscosity of the inventive composition is preferably in the range of 1 to 200 cps, more preferably in the range of 10 to 150 cps as preferably measured by a Brookfield viscometer, preferably Model LVDV-II+, and with a Spindle No. 1, 50 rpm, at 25° C., preferably measured after 30 sec.

The invention will now be described in greater detail by way of the following non-limiting examples. The examples are for illustrative purposes only and not intended to limit the invention in any way. Physical test methods are described below:

Except in the operating and comparative examples, or where otherwise explicitly indicated, all numbers in this description indicating amounts or ratios of materials or conditions of reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

All percentages in the specification and examples are intended to be by weight unless stated otherwise.

Example 1

A series of inventive and comparative examples were made according to Tables 1 and 2 respectively using the procedure described below in order to evaluate clarity, stability and skin feel.

TABLE 1

Inventive examples:

|  |  |  |  |  | D | E | F | G |
|---|---|---|---|---|---|---|---|---|
|  |  |  |  |  | \multicolumn{4}{c}{Stability} |
|  |  |  |  |  | Stable | Stable | Stable | Stable |
|  |  |  |  |  |  | Rinsing |  |  |
|  |  |  |  |  | Fast | Fast | Fast | Fast |
|  |  |  |  |  |  | HLB(AVE) |  |  |
|  |  |  |  |  | 11.29 | 11.29 | 11.29 | 11.29 |
|  | chemical name | HLB | MIU | MW | WT. % | WT. % | WT. % | WT. % |
| oil | Mineral Oil |  | 0.37 | — | 34.05 | 30.05 | 30.05 | 30.05 |
| Fatty esters | ISODECYL NEOPENTANOATE |  | 0.15 | 242.4 | 5 | 30 |  |  |
|  | ETHYLHEXYL ISONONANOATE |  | 0.15 | 270.4 |  |  | 30 |  |
|  | ISOPROPYL MYRISTATE |  | 0.21 | 270.4 | 21 |  |  | 30 |
|  | TRIETHYLHEXANOIN |  | 0.3 | 470.6 |  |  |  |  |
|  | DIETHYLHEXYL SUCCINATE |  | 0.31 | 342.5 |  |  |  |  |
|  | BIS-ETHOXYDIGLYCOL SUCCINATE |  | 0.41 | 350.4 |  |  |  |  |
| Nonionic surfactant | PEG-75 STEARATE | 19 |  |  | 0.5 | 0.5 | 0.5 | 0.5 |
|  | POLYSORBATE 80 | 15 |  |  | 3 | 3 | 3 | 3 |
|  | SORBETH-30 TETRAISOSTEARATE | 11.1 |  |  |  |  |  |  |
|  | PEG-20 Glyceryl Triisostearate | 11 |  |  | 11.1 | 11.1 | 11.1 | 11.1 |
|  | Sorbitan Isostearate | 9 |  |  |  |  |  |  |
|  | PEG-20 Hydrogenated Castor Oil Isostearate | 8 |  |  | 3.6 | 3.6 | 3.6 | 3.6 |
| Polyol | Propylene glycol |  |  |  | 14.5 | 14.5 | 14.5 | 14.5 |
|  | C12-C20 n-alkyl Fatty acid(s) |  |  |  | 0.3 | 0.3 | 0.3 | 0.3 |
|  | Water |  |  |  | 6 | 6 | 6 | 6 |
| Additives | perfume, colors, preservatives, pH adjusters etc. |  |  |  | 0.95 | 0.95 | 0.95 | 0.95 |
|  | Total |  |  |  | 100 | 100 | 100 | 100 |

TABLE 2

Comparative examples.

| | | | | | A | B | C | H | J | J | K |
|---|---|---|---|---|---|---|---|---|---|---|---|
| | | | | | Stability | | | | | | |
| | | | | | Stable | Stable | Stable | un-stable | un-stable | un-stable | un-stable |
| | | | | | Rinsing | | | | | | |
| | | | | | Slow | Slow | Slow | N/A | N/A | N/A | N/A |
| | | | | | HLB(AVE) | | | | | | |
| | | | | | 10.63 | 10.63 | 10.63 | 11.29 | 11.29 | 11.29 | 11.29 |
| | chemical name | HLB | MIU | MW | WT. % | WT. % | WT. % | WT. % | WT. % | WT. % | WT. % |
| oil | Mineral Oil | | 0.37 | — | 29.25 | 33.25 | 29.25 | 30.05 | 30.05 | 30.05 | 60.05 |
| Fatty esters | ISODECYL NEOPENTANOATE | | 0.15 | 242.4 | 30 | 5 | | | | | |
| | ETHYLHEXYL ISONONANOATE | | 0.15 | 270.4 | | | | | | | |
| | ISOPROPYL MYRISTATE | | 0.21 | 270.4 | | 21 | 30 | | | | |
| | TRIETHYLHEXANOIN | | 0.3 | 470.6 | | | | 30 | | | |
| | DIETHYLHEXYL SUCCINATE | | 0.31 | 342.5 | | | | | 30 | | |
| | BIS-ETHOXYDIGLYCOL SUCCINATE | | 0.41 | 350.4 | | | | | | 30 | |
| Nonionic surfactant | PEG-75 STEARATE | 19 | | | | | | 0.5 | 0.5 | 0.5 | 0.5 |
| | POLYSORBATE 80 | 15 | | | | | | 3 | 3 | 3 | 3 |
| | SORBETH-30 TETRAISOSTEARATE | 11.1 | | | 5 | 5 | 5 | | | | |
| | PEG-20 Glyceryl Triisostearate | 11 | | | 11 | 11 | 11 | 11.1 | 11.1 | 11.1 | 11.1 |
| | Sorbitan Isostearate | 9 | | | 1.5 | 1.5 | 1.5 | | | | |
| | PEG-20 Hydrogenated Castor Oil Isostearate | 8 | | | 1.5 | 1.5 | 1.5 | 3.6 | 3.6 | 3.6 | 3.6 |
| Polyol | Propylene glycol | | | | 14.5 | 14.5 | 14.5 | 14.5 | 14.5 | 14.5 | 14.5 |
| | C12-C20 n-alkyl Fatty acid(s) | | | | 0.3 | 0.3 | 0.3 | 0.3 | 0.3 | 0.3 | 0.3 |
| | Water | | | | 6 | 6 | 6 | 6 | 6 | 6 | 6 |
| Additives | perfume, colors, preservatives, pH adjusters etc. | | | | 0.95 | 0.95 | 0.95 | 0.95 | 0.95 | 0.95 | 0.95 |
| | Total | | | | 100 | 100 | 100 | 100 | 100 | 100 | 100 |

Based on the results reported in Tables 1 and 2, it is evident that clarity, stability and skin feel sensory results was generally better for the inventive samples when compared to the comparative samples.

Example 2

Selected comparative and inventive compositions described in Tables 1 and 2 were tested by an expert test panel for perception of skin feel after rinsing according to the procedure described below and the results are shown in Table 3.

TABLE 3

| Rinsing test results | | | | | | |
|---|---|---|---|---|---|---|
| | A | B | C | D | E | G |
| Results | Slow | Slow | Slow | Fast | Fast | Fast |
| | Slow | Slow | Slow | Fast | Fast | Fast |
| | Moderate | Moderate | Slow | Fast | Fast | Fast |
| | Moderate | Moderate | Moderate | Fast | Fast | Fast |

Expert panel who can assess rinsing speed accurately has been screened by Pre-test from 10 experts.

Assessed 4 replicates by expert panel.
Whole face, Home in use. Blind, 1 day usage/1 product
Evaluated speed of rinsing by 3 point scale
(1: slow, 2: moderate and 3: fast)
a. Preparation of the examples illustrated in Tables 1-2:
   1. Weigh all raw materials except for perfume in a beaker as appropriate.
   2. Heat beaker contents to 85 C in a hot water bath to 90 C and hold for 10 min.
   3. Blend gently via stirring for 5 min with a stirring rod.
   4. Cool the beaker contents to 45 C.
   5. Add Perfume and gently resume stirring for 5 min.
b. MIU frictional coefficient measurement method
   Measurement Method of Friction in the Present Invention
   1) A drop of the compound to be tested (0.1 mL) is applied on artificial leather*.
   2) Measurement is started according to the following conditions.
   Measurement Conditions
   Apparatus: Friction Tester KES-SE (Kato Tech Co., Ltd.)
   Temperature: 25+/−3° C.
   Humidity: 65+/−3% RH (Relative humidity)
   Load: 25 g
   Detector: Silicone sensor
   Artificial Leather: Tricot whose surface is treated with polyurethane and coated with collagen. Supplier:

Idemitsu Technofine Co., Ltd. (Japan)/Ideatex Japan Co Ltd. This is available under the tradename Sapulale.

Figure 3:
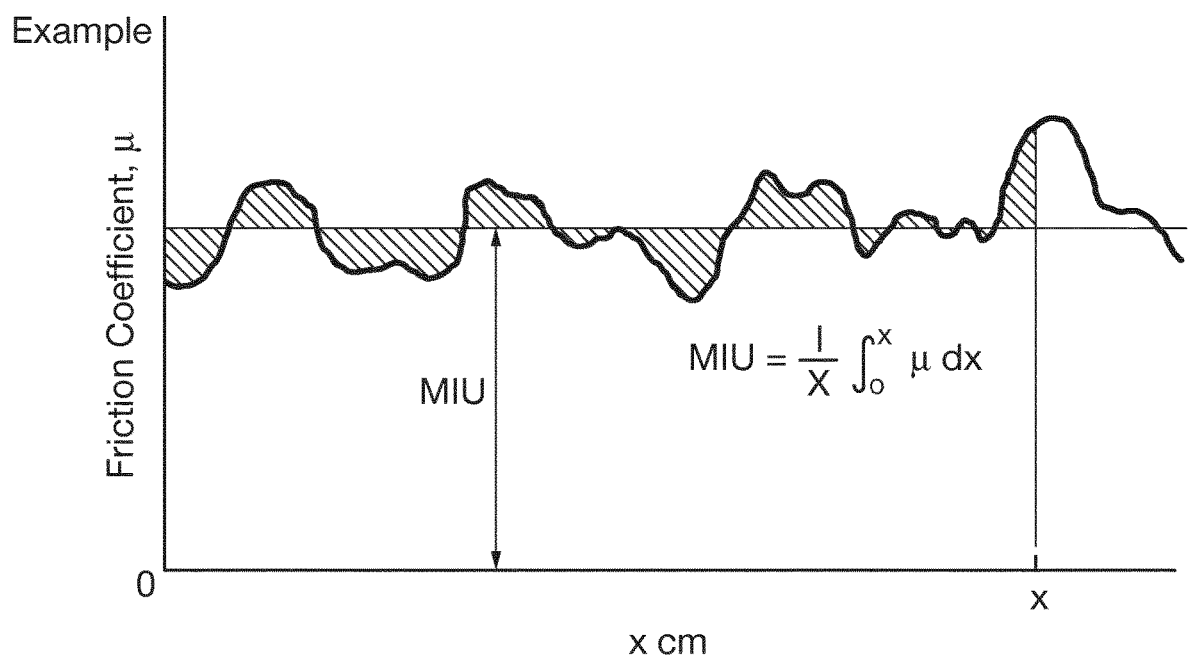
FIG. 3 is graphical diagram demonstrating how the MIU frictional value is calculated using the KES-SE friction tester depicted in FIG. 2.

3. MIU is calculated via the graphical method illustrated in FIG. 3. The friction μ measured over a distance x, equals $$\frac{1}{X}\int_0^x \mu dx$$

The number of "MIU" is automatically provided by the KES-SE friction tester. The number of X is the actual distance of continuous measurement which affect to measurement accuracy. This equation exemplifies that the average of the friction coefficient equals MIU, derived from a continuous friction coefficient measurement. As known in the art, by dividing the integrated value by the monitoring width X, the mean coefficient of friction MIU is obtained.

The foregoing description and examples illustrate selected embodiments of the present invention. In light thereof variations and modifications will be suggested to one skilled in the art, all of which are within the scope and spirit of this invention.

The invention claimed is:

1. A cleansing composition comprising:
   a. 10 to 25 wt. % of nonionic surfactant(s) collectively having a weight average HLB greater than 10.8,
      wherein HLB average is L(nonionic surfactant HLB× concentration)/total nonionic surfactant concentration),
      wherein nonionic surfactants do not include linear and/or branched $C_5$-$C_{20}$
   alkyl ester(s) with a molecular weight of 320 or below;
   b. 20 to 40 wt. % of linear and/or branched $C_5$ to $C_{20}$ alkyl mono ester(s) where the molecular weight of the ester(s) is/are less than 320, wherein the alkyl monoester(s) comprises isopropyl myristate;
   C. 25 to 40 wt. % of hydrocarbon oil(s);
   d. 8 to 20 wt. % polyol(s); and
   e. 1 to 8% wt. % of water.

2. The composition of claim 1, wherein the alkyl mono ester(s) have an average frictional coefficient upon application to the skin of less than 0.3, where the MIU is measured by the standard friction coefficient method using KES-SE friction tester.

3. The composition of claim 1 further comprising less than 1.0 wt. % of silicone oil(s).

4. The composition of claim 1 wherein the alkyl monoester(s) is isopropyl myristate.

5. The composition of claim 1 wherein at least 50 wt. % the total polyol(s) are selected from propylene glycol, 1,3-butylene glycol, dipropylene glycol or blends thereof.

6. The composition of claim 1 wherein the composition is transparent.

7. The composition of claim 1 wherein the composition has a viscosity in the range of 1 to 200 cps at 25 C as measured by Brookfield method, spindle 1, 50 rpm.

8. The composition of claim 1 wherein the composition is a make-up remover composition.

9. A packaged product for removing makeup from the skin comprising the composition of claim 1 contained within a pump dispenser.

10. The composition of claim 1 wherein the composition further comprises glycerine.

* * * * *